United States Patent
Seo et al.

(10) Patent No.: US 7,571,077 B2
(45) Date of Patent: Aug. 4, 2009

(54) METHOD FOR EVALUATING ANTI-CONTAMINATION LEVEL ON A SURFACE OF OPTICAL RECORDING MEDIUM, THE APPARATUS AND THE OPTICAL RECORDING MEDIUM

(75) Inventors: Hun Seo, Yongin-si (KR); Seung Yoon Lee, Seoul (KR); Jin Hong Kim, Gyeonggi-do (KR); Jin Yong Kim, Seongnam-si (KR)

(73) Assignee: LG Electronics, Inc., Seoul (KR)

( * ) Notice: Subject to any disclaimer, the term of this patent is extended or adjusted under 35 U.S.C. 154(b) by 863 days.

(21) Appl. No.: 10/986,032

(22) Filed: Nov. 12, 2004

(65) Prior Publication Data

US 2005/0106354 A1 May 19, 2005

(30) Foreign Application Priority Data

Nov. 14, 2003 (KR) .................. 10-2003-0080601

(51) Int. Cl.
  *G06F 11/30* (2006.01)
(52) U.S. Cl. .................. 702/183; 702/69; 369/53.15
(58) Field of Classification Search .................. None
  See application file for complete search history.

(56) References Cited

U.S. PATENT DOCUMENTS 5,485,444 A * 1/1996 Kuhn et al. .............. 369/53.15
6,600,715 B2 * 7/2003 Okumura et al. .......... 369/275.1
7,092,091 B2 * 8/2006 Itoh et al. .................. 356/338
2004/0234720 A1 * 11/2004 Hayashida et al. ......... 428/64.4

FOREIGN PATENT DOCUMENTS

| EP | 0671742 | 9/1995 |
| EP | 1 610 317 | 12/2005 |
| JP | 05-089461 | 4/1993 |
| JP | 05-314477 | 11/1993 |
| JP | 2003-22569 | 1/2003 |
| JP | 2003-168248 | 6/2003 |
| JP | 2004-281010 | 10/2004 |
| WO | WO 03/029382 A1 * | 4/2003 |
| WO | WO 2004/084206 A1 * | 9/2004 |

OTHER PUBLICATIONS

International Search Report issued Feb. 13, 2007 in related International Application No. PCT/KR2004/002937.
Office Action issued May 9, 2008 by the Japanese Patent Office in counterpart Japanese Patent Application No. 2006-539394.
Search Report for European patent application No. 04 800 088.9 dated Mar. 5, 2009.

* cited by examiner

Primary Examiner—Manuel L Barbee
(74) Attorney, Agent, or Firm—Harness, Dickey & Pierce

(57) ABSTRACT

A method for evaluating an anti-contamination level on a surface of optical recording medium is disclosed. The method includes forming an artificial fingerprint on the surface by contacting a stamp having an artificial material adhered thereto on an optical recording medium, and measuring a symbol error rate (SER) of the formed artificial fingerprint, to determine a sensitivity of the fingerprint and determining whether the optical recording medium is of good quality or bad quality depending upon the measured SER.

23 Claims, 4 Drawing Sheets

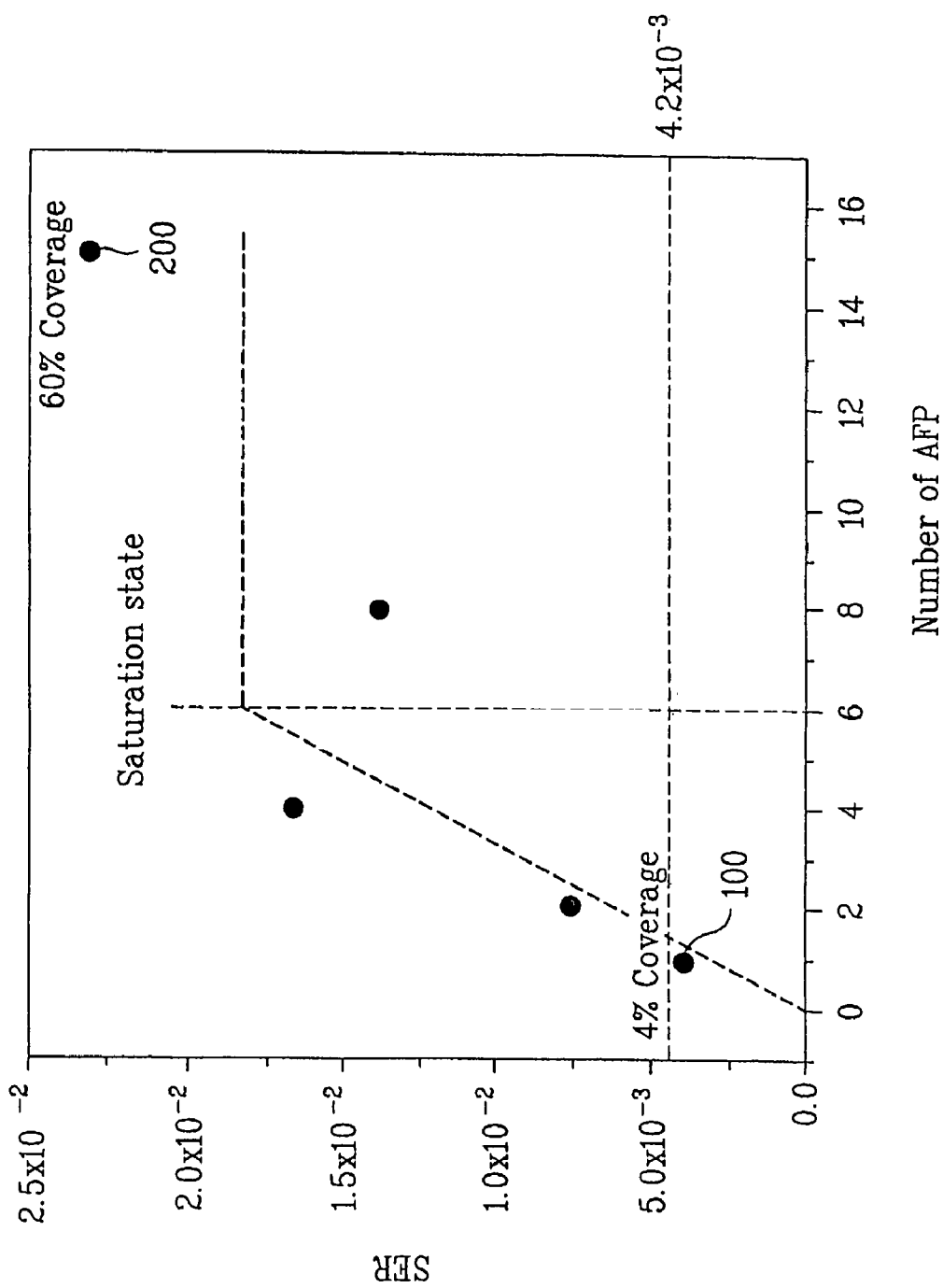

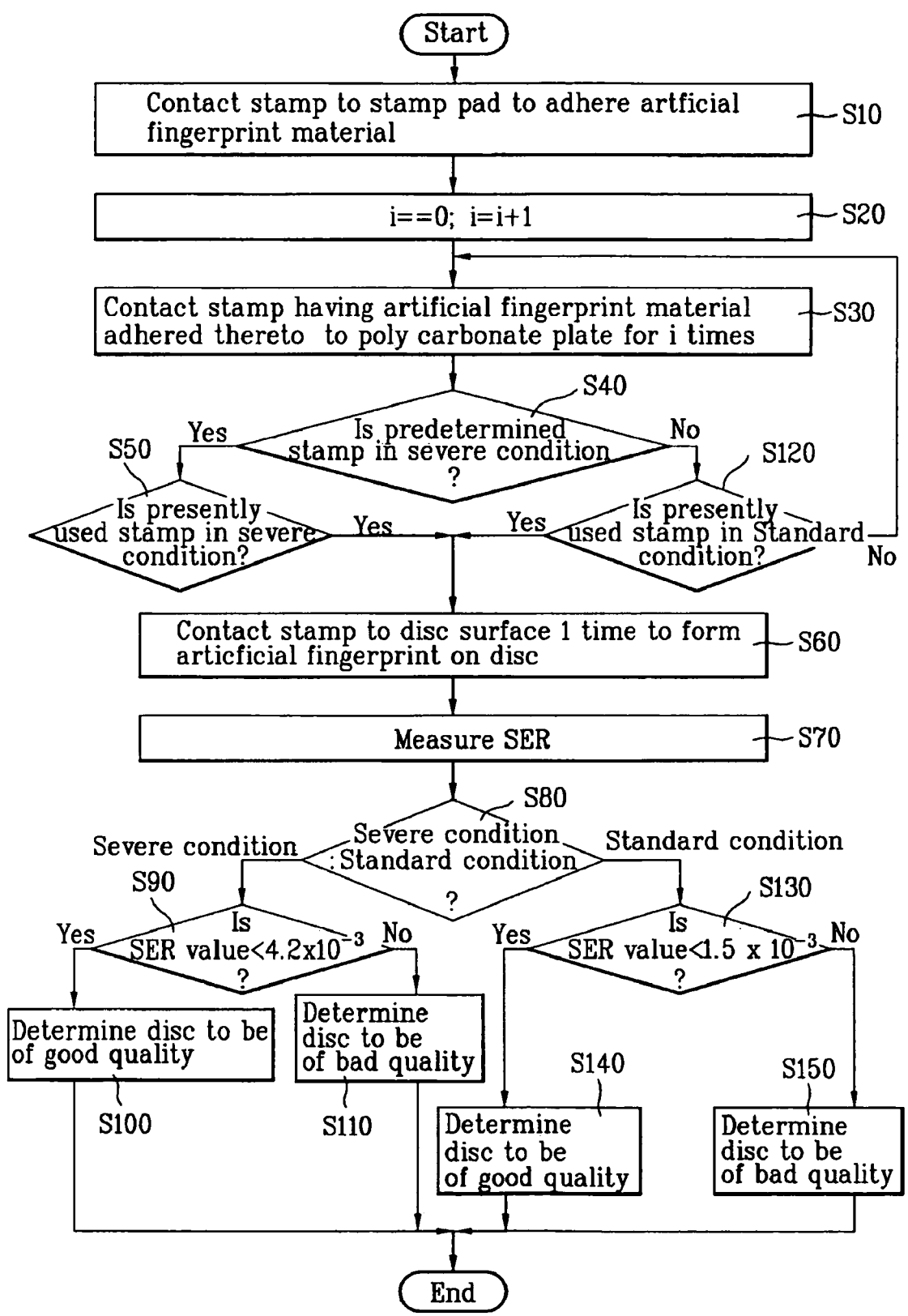

METHOD FOR EVALUATING ANTI-CONTAMINATION LEVEL ON A SURFACE OF OPTICAL RECORDING MEDIUM, THE APPARATUS AND THE OPTICAL RECORDING MEDIUM

This application claims the benefit of the Korean Patent Application No. 10-2003-0080601, filed on Nov. 14, 2003, which is hereby incorporated by reference as if fully set forth herein.

BACKGROUND OF THE INVENTION

1. Field of the Invention

The present invention relates to an optical recording medium such as an optical disc, and more particularly, to a method for evaluating anti-contamination level on a surface of the optical disc. Although the present invention is suitable for a wide scope of applications, it is particularly suitable for quantizing the characteristic of a protective coating film being formed on the surface of an optical disc, so as to enhance the stability thereof.

2. Discussion of the Related Art

Generally, an optical disc is used for recording information on the surface of the optical disc by using laser beam. More specifically, the optical disc is a high-capacity data storage means having audio, video, and text information converted to digital signals, then, a low intensity laser beam is projected thereto so as to carry out a reading of the optical disc by acknowledging the different intensities of the reflected light. Optical disc media include compact discs (CDs), digital video discs (DVDs), laser discs (LDs), and so on. And, recently, blu-ray discs (BDs) and advanced optical discs (AODs) have been in active and competitive development as a standard for the next generation storage means.

The blue-ray disc has been under development to target the high definition video disc recorder (HDVDR). The blu-ray disc is considered to be the next generation optical disc storage means using a bluish-purple semiconductor laser (BPSL). Accordingly, the blu-ray disc has a storage capacity of 27 gigabytes (GB), which corresponds to a 13-hour running time of regular film and a two-hour running time of visual material having high definition television (HDTV) picture quality. As described above, interest and focus on the blu-ray disc as the next generation storage means that can compensate the shortcomings of the conventional DVDs are elevating. However, due to the fine signal characteristics of the blu-ray disc, quality deficiency resulting from scratches, deformities or formation deficiencies, fingerprints, adhesion of impurities during fabrication process, and so on may occur. Therefore, after the fabrication of the blu-ray disc is completed, a quality inspection process is performed, and the inspected product is then shipped to the market.

Generally, the related art optical disc quality inspection process is performed by four (4) measuring drives. Provided that a plurality of optical discs fabricated from the same fabrication device all have the same characteristics, the manufacturer randomly selects an optical disc and mounts the selected optical disc on the measuring system. The first measuring drive measures high frequency signals and jitter from the optical disc. The second measuring drive measures servo signals (i.e., focusing error signals and tracking error signals) based on signals reproduced from the optical disc. The third measuring drive detects the mechanical characteristics of the optical disc presently being under quality inspection. Finally, the last (or fourth) measuring drive detects the optical characteristics of the optical disc.

As described above, the related art optical disc quality inspection process consists of inspecting the accuracy in information recording, the mechanical and optical characteristics of the optical disc, and so on. Chemical and physical contamination, such as fingerprints, that may occur on an incident surface of a laser beam for recording/reproducing information, during the usage of the high density optical disc, may result in a deterioration of optical disc signals, damage in data, as well as incapacity of recording and/or reproducing information on the disc. Therefore, in order to prevent such problems from occurring, a protective coating film is formed on the surface of the disc, so as to enhance the level of anti-contamination or surface stability, and the optical disc is inserted in a cartridge so as to protect the disc from contamination. Recently, however, discs having only the protective coating film formed thereon and no cartridges, in order to minimize the volume of the disc, have been introduced to the market. Therefore, the quantization of anti-contamination of the protective coating film formed on the surface of the disc has become an important factor for effective fabrication and usage of a disc.

Nevertheless, a quantized method for evaluating anti-contamination occurring on the surface of a high density optical disc has not been developed in the related art. In the related art, the level of anti-contamination is evaluated solely by the personal judgment of an extensively experienced manufacturer, whose judgment is based on observing the amount or level of an actual fingerprint or a contaminant being adhered or smeared to the surface of the disc. Therefore, when inspected through the above-described related art anti-contamination level evaluation method, some misjudgment may occur and deficient discs that were subject to such misjudgment may be shipped to the consumer market.

SUMMARY OF THE INVENTION

Accordingly, the present invention is directed to a method for evaluating an anti-contamination level on a surface of the optical disc that substantially obviates one or more problems due to limitations and disadvantages of the related art.

An object of the present invention is to provide a method for evaluating an anti-contamination level on a surface of the optical disc that can quantize the characteristics of a protective coating film formed to enhance stability of the surface of the optical disc.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a method for evaluating an anti-contamination level on an optical recording medium includes forming an artificial fingerprint on a surface of the optical recording medium by contacting a stamp having an artificial material adhered thereto on an optical recording medium; and measuring a symbol error rate (SER) in an area where the artificial fingerprint is formed, to determine a sensitivity for fingerprint.

The artificial fingerprint material may be formed of at least any one of water, methanol, sodium chloride (NaCl), urea, lactic acid, and violet dye. The stamp may be formed of Si(Silicone)-rubber and may have a diameter of approximately 10 millimeters (mm). The stamp may contact the disc with a pressure of 500 grams (g).

In another aspect of the present invention, a method for evaluating an anti-contamination level on a surface of optical recording medium includes (a) contacting a stamp with predetermined pressure on a stamp pad on which an artificial fingerprint material is formed and adhering the artificial fingerprint material on the stamp; (b) contacting the stamp having the artificial fingerprint material on a surface of optical recording medium to form an artificial fingerprint on the surface; and (c) determining a sensitivity of the fingerprint depending upon a symbol error rate (SER) on the location where the artificial fingerprint is formed.

In another aspect of the present invention, a method for evaluating an anti-contamination level on a surface of optical recording medium further includes controlling a number of contacting times of the stamp having the artificial stamp material adhered thereon from step (a) to a dummy, according to a severe condition or a standard condition.

Herein, the stamp may be in a severe condition when the number of contacting times from the stamp to the dummy is between 0 and 1, and the stamp may be in a standard condition when the number of contacting times from the stamp to the dummy is between 2 and 4. When the stamp is in a severe condition, the step (c) includes determining the optical recording medium as being of good quality when the SER is less than $4.2 \times 10^{-3}$, and determining the optical recording medium as being of bad quality when the SER is more than or equal to $4.2 \times 10^{-3}$. On the other hand, when the stamp is in a standard condition, the step (c) includes determining the optical recording medium as being of good quality when the SER is less than $1.5 \times 10^{-3}$, and determining the optical recording emdium as being of bad quality when the SER is more than or equal to $1.5 \times 10^{-3}$.

In a further aspect of the present invention, an optical recording medium is same kind of an optical recording medium evaluated by the above method.

In a further aspect of the present invention, an apparatus for evaluating an anti-contamination level on an optical recording medium includes a stamp for forming an artificial fingerprint on a surface of the optical recording medium by contacting the stamp having an artificial material adhered thereto on an optical recording medium; and a measuring unit for measuring a symbol error rate (SER) in an area where the artificial fingerprint is formed, to determine a sensitivity for fingerprint.

Herein, wherein the step (b) contacts the stamp on the surface of optical recording medium until the artificial fingerprint being formed on the surface covers at least 50% of one long distance code (LDC) block of the optical recording medium, the step (c) may include determining the optical recording medium as being of good quality when the SER is less than $4.2 \times 10^{-3}$, and determining the optical recording medium as being of bad quality when the SER is more than or equal to $4.2 \times 10^{-3}$.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings:

FIG. 2 illustrates a graph showing a symbol error rate (SER) in relation with a number of times a stamp is being contacted to a dummy according to the present invention;

FIG. 3 illustrates a method for evaluating anti-contamination level on a disc surface according to a first embodiment of the present invention.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1A:
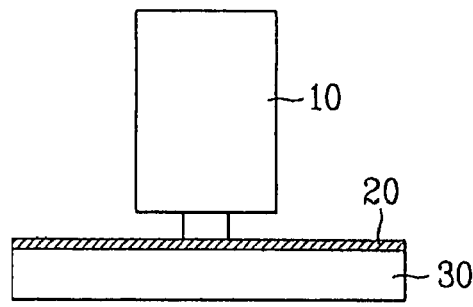
FIGS. 1A to 1D illustrate process steps of a method for evaluating anti-contamination level on a disc surface.
Figure 1B:
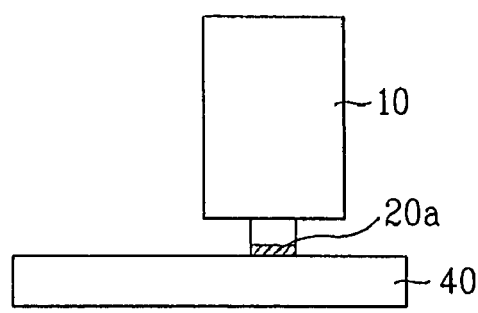
Figure 1C:
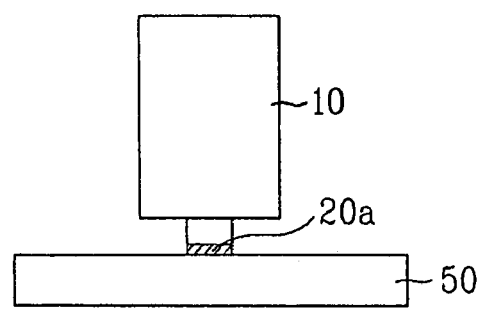
Figure 1D:
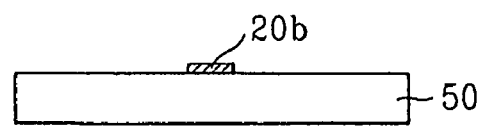

FIGS. 1A to 1D illustrate process steps of a method for evaluating anti-contamination level on a disc surface. Referring to FIG. 1A, a stamp 10 for forming an artificial fingerprint is contacted to a stamp pad 30 at least once, the stamp having an artificial fingerprint material formed thereon, thereby adhering the artificial fingerprint material to the stamp 10 being contacted to the stamp pad 30. Subsequently, the stamp 10 having the artificial fingerprint material 20a adhered thereto is contacted to a dummy at least once, as shown in FIG. 1B, thereby preventing the artificial fingerprint material 20a from being excessively adhered to the stamp 10. Depending upon the number of times the stamp 10 contacts the dummy 40, the stamp 10 can be classified into a severe condition and a standard condition. The stamp 10 having contacted the dummy 40 for a predetermined number of times, as shown in FIG. 1C, then contacts a disc 50 having a protective coating film formed thereon, thereby adhering an artificial fingerprint 20b on the surface of the disc 50. At this point, it is preferable that the dummy is formed of a polycarbonate plate. Thereafter, referring to FIG. 1D, a symbol error rate (SER) of the artificial fingerprint (20b) formed on the surface of the disc 50 is measured, thereby determining a sensitivity of the fingerprint or classifying the manufactured disc into good quality and defective (or bad quality).

The SER is determined as the number of erroneous bytes in the related data block divided by the total number of bytes in those data blocks. In Blu-ray system, the SER is determined as the number of erroneous bytes in the related long distance code (LDC) Block divided by the total number of bytes in those LDC Blocks.

Referring to FIG. 2, the quality of the manufactured disc 50 is determined and categorized depending upon the number of artificial fingerprints 20b formed on the surface of, the disc 50 by the stamp 10 and the relation of the number of artificial fingerprints 20b with the symbol error rate (SER). More specifically, FIG. 2 illustrates data showing variations of the symbol error rate (SER) in accordance with the number of artificial fingerprints having a diameter of 10 millimeters (mm) being formed on the surface of a random blu-ray disc having a radius of 40 millimeters (mm). When only one artificial fingerprint 100 is formed on the surface of the disc, approximately 4% of the entire track of the disc is covered. And, when 15 artificial fingerprints 200 are formed on the surface of the disc, approximately 60% of the entire track of the disc is covered.

In addition, when 6 or more artificial fingerprints are formed on the surface of the disc, the SER becomes saturated (or in a saturation state). More specifically, 6 or more artificial fingerprints are sufficient enough to cover one entire long distance code (LDC) block. In the present invention, based on the SER results shown, under a set of conditions, during the inspection described in FIG. 2, a manufactured disc is determined to be of good quality when the SER is less than $4.2 \times 10^{-3}$ and of bad quality when the SER is more than or equal to $4.2 \times 10^{-3}$. The method for evaluating an anti-contamination level on a disc surface will now be described in detail with the following drawings.

First Embodiment

FIG. 3 illustrates a method for evaluating anti-contamination level on a disc surface according to a first embodiment of the present invention. Referring to FIG. 3, the stamp for forming artificial fingerprints is contacted at least once on the stamp pad having the artificial fingerprint material formed thereon, so as to adhere the artificial fingerprint material on the stamp (S10). Herein, the artificial fingerprint material is formed of at least any one of water, methanol, sodium chloride (NaCl), urea, lactic acid, and a very small amount of violet dye. In addition, the stamp is formed of Si-Rubber, and it is preferable that the stamp having the artificial fingerprint material adhered thereto has a diameter of about 10 millimeters (mm). Then, the stamp having a pressure of 500 grams (g) is contacted to the stamp pad.

Subsequently, the stamp having the artificial fingerprint material formed thereon is contacted at least once to the dummy (i.e., the polycarbonate plate), so as to prevent the artificial fingerprint material from being excessively adhered to the stamp (S20 to S30). At this point, the stamp also contacts the dummy with a pressure of 500 grams (g), and depending upon the number of contacting times of the stamp to the dummy, the condition of the stamp is classified into a severe condition and a standard condition. More specifically, when the number of contacts is between 0 and 1, as shown in Table 1 below, the stamp is determined to be in severe condition, and when the number of contacts is between 2 and 4, then, the stamp is determined to be in standard condition. Such conditions are not limited to the number of contacts described in Table 1 and can be varied by the inspector evaluating the anti-contamination level on the disc surface.

TABLE 1

| Number of Contacts | Condition |
| --- | --- |
| 0 | Severe |
| 1 | |
| 2 | Standard |
| 3 | |
| 4 | |

Therefore, upon evaluating the anti-contamination level on the disc surface, when the condition of the stamp is set to the standard condition, the number of contact times from the stamp to the dummy is increased to between 2 and 4 times, thereby setting the stamp to the standard condition (S120). Subsequently, the stamp having contacted the dummy for a predetermined number of times is contacted to the disc having the protective coating film formed thereon for only one time with a pressure of 500 grams (g), thereby forming the artificial fingerprint on the surface of the disc (S60). At this point, it is preferable to form the dummy of a polycarbonate plate. Thereafter, the SER of the artificial fingerprint formed on the disc is measured, so as to determine the quality of the disc (i.e., either good or bad) through an evaluation of the anti-contamination level (S70). Herein, the quality of the disc, i.e., whether the disc is of good quality or of bad quality, varies depending upon whether the stamp is in a severe condition or a standard condition (S80).

Depending upon the result from the above-described process (S80), and when the stamp being presently used is in a severe condition, the disc is determined to be of good quality if the SER value of the artificial fingerprint being formed on the surface of the disc is less than $4.2 \times 10^{-3}$ (S100). On the other hand, the disc is determined to be of bad quality if the SER value of the disc is more than or equal to $4.2 \times 10^{-3}$ (S110). Furthermore, depending upon the result from the above-described process (S80), and when the stamp being presently used is in a standard condition, the disc is determined to be of good quality if the SER value of the artificial fingerprint being formed on the surface of the disc is less than $1.5 \times 10^{-3}$ (S140). On the other hand, the disc is determined to be of bad quality if the SER value of the disc is more than or equal to $1.5 \times 10^{-3}$ (S150).

When the stamp is in a standard condition, the reference evaluation value is set to $1.5 \times 10^{-3}$ because an error may occur during the process of determining the quality of the manufactured disc if the reference evaluation value of the artificial fingerprint being formed once on the surface of the disc, when the stamp is in a severe condition, and the reference evaluation value of the artificial fingerprint being formed once on the surface of the disc, when the stamp is in a standard condition, are set to be identical. Accordingly, by setting the reference evaluation value in the standard condition to ⅓ of the reference evaluation value in the severe condition, a similar anti-contamination evaluation level can be obtained.

Second Embodiment

Figure 4:
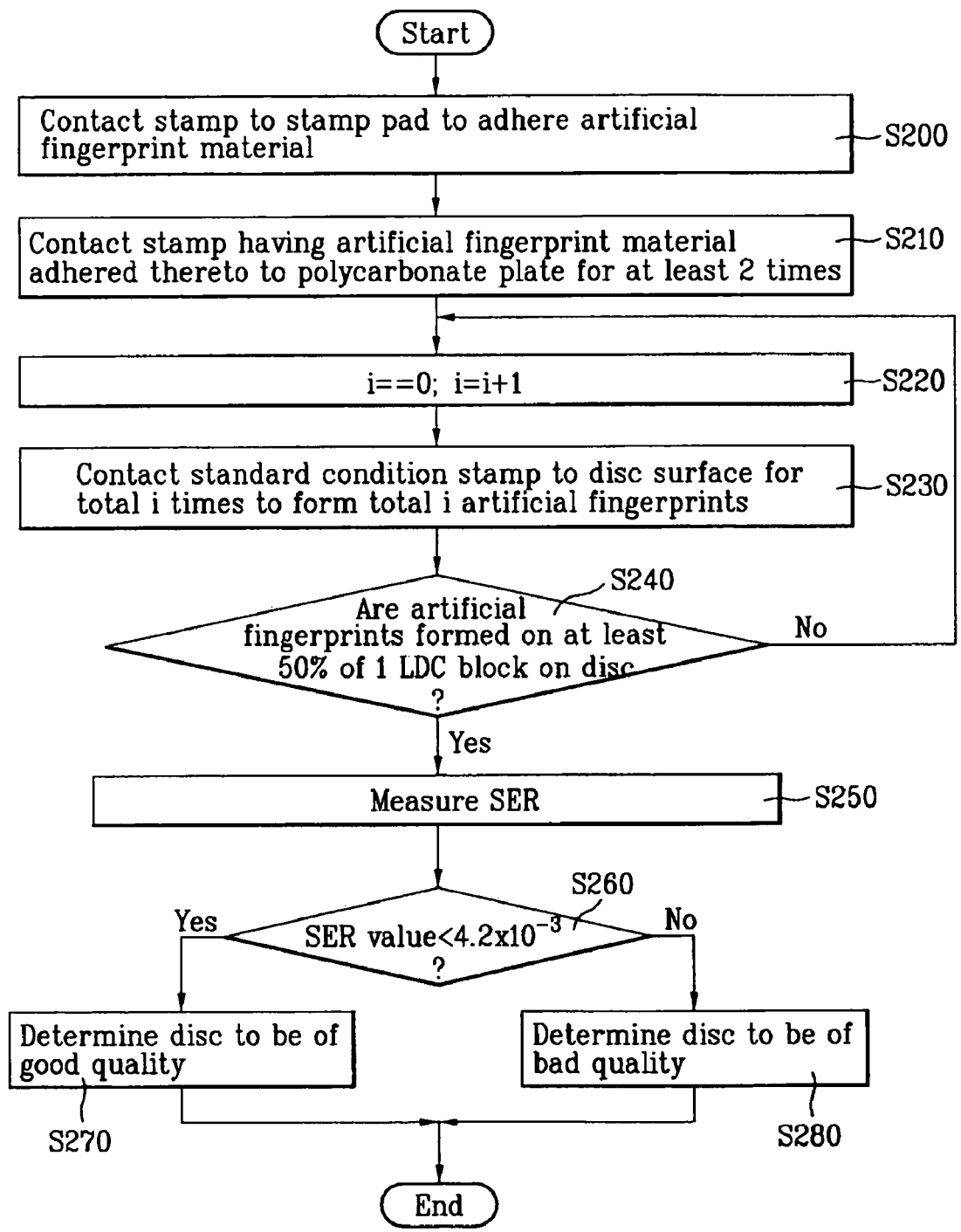
FIG. 4 illustrates a method for evaluating anti-contamination level on a disc surface according to a second embodiment of the present invention.

FIG. 4 illustrates a method for evaluating anti-contamination level on a disc surface according to a second embodiment of the present invention. Referring to FIG. 4, the stamp for forming artificial fingerprints is contacted at least once on the stamp pad having the artificial fingerprint material formed thereon, so as to adhere the artificial fingerprint material on the stamp (S200). Herein, the artificial fingerprint material is formed of at least any one of water, methanol, sodium chloride (NaCl), urea, lactic acid, and a very small amount of violet dye. In addition, the stamp is formed of Si-Rubber, and it is preferable that the stamp having the artificial fingerprint material adhered thereto has a diameter of about 10 millimeters (mm). Then, the stamp having a pressure of 500 grams (g) is contacted to the stamp pad.

Subsequently, the stamp having the artificial fingerprint material formed thereon is contacted at least 2 times and not more than 4 times to the dummy (i.e., the polycarbonate plate), so as to prevent the artificial fingerprint material from being excessively adhered to the stamp, thereby forming a stamp in a standard condition (S210). At this point, the stamp also contacts the dummy with a pressure of 500 grams (g). Then, the stamp having contacted the dummy for a predetermined number of times is contacted to the disc having the protective coating film formed thereon with a pressure of 500 grams (g), thereby forming the artificial fingerprint on the surface of the disc (S230). Afterwards, the number of contacts from the stamp to the surface of the disc is increased, so that the artificial fingerprints formed on the surface of the disc cover at least 50% of one long distance code (LDC) block of the disc.

Herein, the SER is increased (or elevated) as the number of artificial fingerprints within the one LDC block increases. Accordingly, a sufficient number of artificial fingerprints should be formed to cover at least 50% of one LDC block in order to evaluate an accurate anti-contamination level. For example, when the disc has a radius of 40 millimeters (mm), the artificial fingerprints that are formed in one LDC block on the disc should be formed at least 3 times with ¼ of the circumference of the disc, in order to cover at least 50% of the one LDC block. Subsequently, after measuring the SER value of the artificial fingerprint being formed on the surface of the disc, the quality of the disc (i.e., either good or bad) is determined through the evaluation of the anti-contamination level (S250). Then, the disc is determined to be of good quality when the SER value is less than $4.2 \times 10^{-3}$ (S270), and the disc is determined to be of bad quality when the SER value is more than or equal to $4.2 \times 10^{-3}$ (S280).

Instead of relying on the mere sensation (or personal judgment) of a manufacturer upon the inspection for the contamination level of the disc, the present invention determines the quality of the manufactured disc (i.e., good quality or bad quality) by adhering a contaminant on the surface of the disc, measuring the SER value of the disc, and then determining the quality of the disc.

As described above, the method for evaluating the anti-contamination level of the disc surface according to the present invention has the following advantages. First, a level of surface contamination, which largely affects the quality of a manufactured disc, can be quantized based on an objective reference value and evaluated. In addition, the characteristics of a protective coating film can also be quantized in order to enhance the stability characteristics of the disc surface, thereby improving the reliability of the evaluation result. Finally, the quality of the disc, i.e., whether the disc is of good quality or bad quality, is accurately determined based on an objective reference value, thereby ensuring consistent product characteristics and high reliability from users.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A method for evaluating an anti-contamination level on an optical recording medium, comprising:
    forming an artificial fingerprint on a surface of the optical recording medium by contacting a stamp having an artificial material adhered thereto on the optical recording medium;
    measuring an error rate in an area where the artificial fingerprint is formed; and
    comparing the measured error rate with a reference value to determine a sensitivity for the fingerprint,
    wherein the optical disc is determined to be of good quality if the measured error rate is less than the reference value of $4.2 \times 10^{-3}$.

2. The method of claim 1, wherein the artificial fingerprint material is formed of at least any one of water, methanol, sodium chloride (NaCl), urea, lactic acid, and violet dye.

3. The method of claim 1, wherein the stamp is formed of Si (Silicone)-rubber.

4. The method of claim 1, wherein the stamp has a diameter of approximately 10 millimeters (mm).

5. The method of claim 1, wherein the stamp contacts the disc with a pressure of 500 grams (g).

6. A method for evaluating an anti-contamination level on a surface of optical recording medium, comprising:
    (a) contacting a stamp with a pressure on a stamp pad on which an artificial fingerprint material is formed and adhering the artificial fingerprint material on the stamp;
    (b) contacting the stamp having the artificial fingerprint material on a surface of an optical recording medium to form an artificial fingerprint on the surface; and
    (c) determining a sensitivity to the fingerprint depending upon an error rate on the location where the artificial fingerprint is formed,
    wherein the said determining step determines the sensitivity of the optical recording medium by comparing the measured error rate with a reference value and determines the optical recording medium is of good quality if the measured error rate is less than reference value, the reference value is $4.2 \times 10^{-3}$.

7. The method of claim 6, further comprising:
    controlling a number of times the stamp having the artificial stamp material adhered thereon from step (a) contacts a dummy, according to a severe condition or a standard condition.

8. The method of claim 7, wherein when the stamp is in a severe condition the number of times the stamp contacts the dummy is 0 or 1, and when the stamp is in a standard condition the number of times the stamp contacts the dummy is at or between 2 and 4.

9. The method of claim 7, wherein, when the stamp is in a severe condition, the step (c) includes determining the optical recording medium is of good quality when the error rate is less than $4.2 \times 10^{-3}$ and greater than $1.5 \times 10^{-3}$.

10. The method of claim 7, wherein, when the stamp is in a standard condition, the step (c) includes determining the optical recording medium is of good quality when the error rate is less than $1.5 \times 10^{-3}$.

11. The method of claim 7, wherein the dummy is formed of polycarbonate.

12. The method of claim 6, wherein the artificial fingerprint material is formed of at least any one of water, methanol, sodium chloride (NaCl), urea, lactic acid, and violet dye.

13. The method of claim 6, wherein the stamp is formed of Si (Silicone)-rubber.

14. The method of claim 6, wherein in step (a) the stamp contacts the stamp pad with pressure of 500 grams (g).

15. The method of claim 6, wherein in step (b) the stamp formed in a standard condition contacts the optical recording medium for a set number of times and forms artificial fingerprints on the surface of the optical recording medium.

16. The method of claim 15, wherein, in step (b) the stamp contacts the surface of the optical recording medium until the artificial fingerprint being formed on the surface of the optical recording medium covers at least 50% of one long distance code (LDC) block of the optical recording medium.

17. An apparatus for evaluating an anti-contamination level on an optical recording medium, comprising:
    a stamp configured to form an artificial fingerprint on a surface of the optical recording medium by contacting the stamp having an artificial material adhered thereto on the optical recording medium,
    a measuring unit configured to measure an error rate in an area where the artificial fingerprint is formed; and
    a control unit configured to control the measuring unit and configured to compare the measured error rate with a reference value and to determine the optical recording medium to be of good quality if the measured error rate is less than the reference value, $4.2 \times 10^{-3}$.

18. The apparatus of claim 17, wherein the artificial fingerprint material is formed of at least any one of water, methanol, sodium chloride (NaCl), urea, lactic acid, and violet dye.

19. The apparatus of claim 17, wherein the stamp is formed of Si (Silicone)-rubber.

20. The apparatus of claim 17, wherein the stamp contacts the disc with a pressure of 500 grams (g).

21. An apparatus for evaluating an anti-contamination level on an optical recording medium, comprising:
 a measuring unit configured to measure an error rate in an area where an artificial fingerprint is formed on the optical recording medium, the artificial fingerprint being formed by contacting a stamp having artificial fingerprint material with the optical recording medium; and
 a control unit configured to compare the measured error rate with a reference value and to determine the optical recording medium to be of good quality if the measured error rate is less than the reference value, $4.2 \times 10^{-3}$.

22. A recording medium comprising:
 an entrance surface, having a repulsion with respect to grime, the recording medium subject to be verified by a test to determine whether the surface of the recording medium has a sufficient repulsion, wherein
 the test includes the steps of contacting a stamp having an artificial fingerprint material to a surface of an optical recording medium to form an artificial fingerprint on the surface, measuring an error rate from an area where the artificial finger print is formed; and determining the sensitivity for the fingerprint based on the error rate on the area where the artificial fingerprint is formed,
 wherein the optical disc is determined to be acceptable if the measured symbol error rate is less than the reference value of $4.2 \times 10^{-3}$.

23. The recording medium of claim 22, wherein the stamp is formed of Si (Silicone)-rubber and the stamp has a diameter of about 10 mm.

* * * * *